(12) United States Patent
Yamada et al.

(10) Patent No.: US 10,012,605 B2
(45) Date of Patent: Jul. 3, 2018

(54) X-RAY FLUORESCENCE SPECTROMETER

(71) Applicant: RIGAKU CORPORATION, Tokyo (JP)

(72) Inventors: Yasujiro Yamada, Takatsuki (JP); Shinya Hara, Takatsuki (JP); Makoto Doi, Austin, TX (US)

(73) Assignee: Rigaku Corporation, Akishima-shi, Tokyo (JP)

( * ) Notice: Subject to any disclaimer, the term of this patent is extended or adjusted under 35 U.S.C. 154(b) by 0 days.

(21) Appl. No.: 15/522,944

(22) PCT Filed: Jul. 1, 2016

(86) PCT No.: PCT/JP2016/069689
§ 371 (c)(1),
(2) Date: Apr. 28, 2017

(87) PCT Pub. No.: WO2017/026200
PCT Pub. Date: Feb. 16, 2017

(65) Prior Publication Data
US 2017/0322165 A1    Nov. 9, 2017

(30) Foreign Application Priority Data

Aug. 10, 2015 (JP) .................. 2015-157958

(51) Int. Cl.
*G01N 23/223* (2006.01)
*G01N 23/207* (2018.01)

(52) U.S. Cl.
CPC ......... *G01N 23/223* (2013.01); *G01N 23/207* (2013.01); *G01N 2223/076* (2013.01); *G01N 2223/0766* (2013.01)

(58) Field of Classification Search
None
See application file for complete search history.

(56) References Cited

U.S. PATENT DOCUMENTS 6,668,038 B2   12/2003   Kataoka et al.
7,961,842 B2    6/2011   Kawahara et al.
(Continued)

FOREIGN PATENT DOCUMENTS

CN   101151524 A    3/2008
CN   101887038 A   11/2010
(Continued)

OTHER PUBLICATIONS

Written Opinion of the International Searching Authority of PCT/JP2016/069689 dated Sep. 13, 2016.
(Continued)

*Primary Examiner* — Hoon Song
(74) *Attorney, Agent, or Firm* — Sughrue Mion, PLLC (57) ABSTRACT

A measurement line evaluation unit (23): calculates, for all of specified measurement lines, estimated measured intensities by theoretical calculation on the basis of a composition and/or a thickness specified for a thin film; changes, by a predetermined amount, only an estimated measured intensity of one measurement line, and obtains quantitative values of the composition and/or the thickness of the thin film after change of the estimated measured intensity, for each changed measurement line, by a fundamental parameter method; and estimates a quantitative error and/or determines possibility of analysis, on the basis of the obtained quantitative values and the specified composition and/or the specified thickness.

2 Claims, 3 Drawing Sheets (56) References Cited

U.S. PATENT DOCUMENTS

2003/0118148 A1* 6/2003 Kataoka .................. G01J 3/443
378/44
2009/0041184 A1 2/2009 Kawahara et al.

FOREIGN PATENT DOCUMENTS

| CN | 103604818 A | 2/2014 |
|---|---|---|
| JP | 2001-050917 A | 2/2001 |
| JP | 2001-356103 A | 12/2001 |

OTHER PUBLICATIONS

International Search Report of PCT/JP2016/069689 dated Sep. 13, 2016.
Ji Ang et al., "Calculation of Fundamental Parameter Procedure", X-Ray Fluorescence Spectrometry, Dec. 31, 2003, pp. 116 to 119 (8 pages total).
Communication dated Jan. 17, 2018 issued by the State Intellectual Property Office of People's Republic of China in counterpart application No. 201680003309.3.
International Preliminary Report on Patentability with the translation of Written Opinion dated Feb. 22, 2018 issued by the International Bureau in PCT/JP2016/069689.

* cited by examiner

Fig. 3

X-RAY FLUORESCENCE SPECTROMETER

CROSS REFERENCE TO THE RELATED APPLICATION

This application is a National Stage of International Application No. PCT/JP2016/069689filed Jul. 1, 2016, claiming priority based on Japanese patent application No. 2015-157958, filed Aug. 10, 2015, the entire disclosure of which is herein incorporated by reference as a part of this application.

BACKGROUND OF THE INVENTION

Field of the Invention

The present invention relates to an X-ray fluorescence spectrometer which irradiates, with primary X-rays, a sample having a single-layer or multi-layer thin film formed independently or on a substrate and which obtains quantitative values of a composition and/or a thickness of the thin film by a fundamental parameter method on the basis of measured intensities of generated secondary X-rays.

Description of Related Art

In X-ray fluorescence analysis, secondary X-rays to be measured, that is, measurement lines are appropriately selected and set depending on the type of a sample to be analyzed. However, in a so-called thin film sample such as a semiconductor wafer and an iron-zinc alloy plated steel sheet, selecting the measurement lines is not easy because both a composition and a thickness of the thin film are analyzed, or the same elements are contained in different layers or a substrate, in some cases. When selection is inappropriate, accurate analysis cannot be performed.

Accordingly, as a conventional technology, there is an X-ray fluorescence spectrometer (see Patent Document 1) below, for example. In this X-ray fluorescence spectrometer, a measurement line evaluation unit: calculates, for each specified measurement line, a first theoretical intensity for a thickness and a composition specified for each layer of a thin film, and a second theoretical intensity for a thickness and a composition after change of the thickness or the content ratio by a predetermined amount; calculates a predetermined thickness accuracy or content ratio accuracy by using the first and second theoretical intensities; and determines possibility of analysis using the specified measurement lines on the basis of the thickness accuracy or the content ratio accuracy, and the possibility of analysis is displayed on a display. Thus, an operator can easily select the measurement lines on the basis of the displayed possibility.

RELATED DOCUMENT

Patent Document

[Patent Document 1] JP Laid-open Patent Publication No. 2001-356103

However, in a case where both a composition and a thickness of a plated layer, which is a thin film, are analyzed and iron is contained as a common element in a substrate and a plated layer, which are different layers, such as a case where a sample is the iron-zinc alloy plated steel sheet, possibility of analysis using specified measurement lines might be incorrectly determined. The reason for that is as follows. In this conventional spectrometer: the first theoretical intensity for the thickness and the composition specified for the plated layer, the second theoretical intensity obtained by changing only the thickness by a predetermined amount, and the second theoretical intensity obtained by changing only the content ratio by a predetermined amount are calculated for each of specified measurement lines; predetermined thickness accuracy and content ratio accuracy are calculated using these theoretical intensities; and the possibility of analysis using the specified measurement lines is determined on the basis of the thickness accuracy and the content ratio accuracy. However, in actuality, change in quantitative value of each of the thickness and the composition does not correspond to intensity change of a single measurement line, but the intensity of each measurement line greatly depends on both the thickness and the composition of the plated layer.

SUMMARY OF THE INVENTION

The present invention has been made in view of the above conventional problems, and an object of thereof is to provide a spectrometer that facilitates selection of appropriate measurement lines and enables accurate analysis, even in the case where both the composition and the thickness of each layer of a thin film are analyzed and the same elements are contained in different layers, in X-ray fluorescence analysis of the thin film sample.

To achieve the above object, a first aspect of the present invention is an X-ray fluorescence spectrometer which irradiates, with primary X-rays, a sample having a single-layer or multi-layer thin film formed independently or on a substrate, and obtains quantitative values of a composition and/or a thickness of the thin film by a fundamental parameter method on the basis of measured intensities of generated secondary X-rays. The spectrometer includes a measurement line evaluation unit configured to estimate a quantitative error and/or to determine possibility of analysis, for analysis using measurement lines which are secondary X-rays of which the intensities are to be measured, and a display control unit configured to cause a display to display the quantitative error and/or the possibility of analysis obtained by the measurement line evaluation unit.

First, the measurement line evaluation unit calculates, for all specified measurement lines, estimated measured intensities by theoretical intensity calculation and apparatus sensitivity on the basis of a composition and/or a thickness specified for the thin film. Next, the measurement line evaluation unit repeats a process of, on the basis of a set of estimated measured intensities obtained by changing, by a predetermined amount, only an estimated measured intensity of one measurement line among a set of the calculated estimated measured intensities, obtaining quantitative values of the composition and/or the thickness of the thin film after change of the estimated measured intensity by the fundamental parameter method, while changing a measurement line of which the estimated measured intensity is to be changed. Next, the measurement line evaluation unit estimates the quantitative error and/or determines the possibility of analysis, on the basis of the obtained quantitative values and the specified composition and/or the specified thickness.

In the X-ray fluorescence spectrometer according to the first aspect: for all the specified measurement lines, the estimated measured intensities are calculated by the theoretical intensity calculation and the apparatus sensitivity on the basis of the composition and/or the thickness specified for the thin film; only the estimated measured intensity of one measurement line is changed by the predetermined amount and the process of obtaining the quantitative values of the composition and/or the thickness of the thin film after change of the estimated measured intensity by the fundamental parameter method is repeated, while changing the measurement line of which the estimated measured intensity is to be changed; and the quantitative error is estimated and/or the possibility of analysis is determined, on the basis of the obtained quantitative values and the specified composition and/or the specified thickness.

That is, by considering the fact that the intensities of the measurement lines greatly depend on both the composition and the thickness of the thin film, the quantitative error is estimated and/or the possibility of analysis is determined. Accordingly, even in the case where both the composition and the thickness of each layer of the thin film are analyzed and the same elements are contained in different layers, selection of appropriate measurement lines is facilitated and accurate analysis can be performed.

A second aspect of the present invention is an X-ray fluorescence spectrometer which irradiates, with primary X-rays, a sample having a single-layer or multi-layer thin film formed independently or on a substrate, and obtains quantitative values of a composition and/or a thickness of the thin film by a fundamental parameter method on the basis of measured intensities of generated secondary X-rays. The spectrometer includes a measurement line evaluation unit configured to estimate a quantitative error and/or determine possibility of analysis, and to select an optimum combination of measurement lines which are secondary X-rays of which the intensities are to be measured, for analysis using the measurement lines, and a display control unit configured to cause a display to display the quantitative error and/or the possibility of analysis, and the optimum combination of the measurement lines obtained by the measurement line evaluation unit.

First, the measurement line evaluation unit calculates, for all the measurement lines of which the intensities can be measured, estimated measured intensities by theoretical intensity calculation and apparatus sensitivity on the basis of a composition and/or a thickness specified for the thin film. Next, the measurement line evaluation unit creates combinations of the measurement lines for obtaining the quantitative values of the composition and/or the thickness of the thin film, from all the measurement lines of which the intensities can be measured. Next, the measurement line evaluation unit repeats, for each combination of the measurement lines, a process of obtaining quantitative values of the composition and/or the thickness of the thin film after change of an estimated measured intensity by the fundamental parameter method on the basis of a set of estimated measured intensities obtained by changing, by a predetermined amount, only the estimated measured intensity of one measurement line among a set of the calculated estimated measured intensities of the measurement lines included in the combination, while changing a measurement line of which the estimated measured intensity is to be changed. Next, the measurement line evaluation unit estimates the quantitative error and/or determines the possibility of analysis, and selects an optimum combination of the measurement lines, on the basis of the obtained quantitative values and the specified composition and/or the specified thickness.

In the X-ray fluorescence spectrometer according to the second aspect: for all the measurement lines of which the intensities can be measured, estimated measured intensities are calculated by the theoretical intensity calculation and the apparatus sensitivity on the basis of the composition and/or the thickness specified for the thin film; the combinations of the measurement lines for obtaining the quantitative values of the composition and/or the thickness of the thin film are created; for each combination of the measurement lines, only the estimated measured intensity of one measurement line is changed by the predetermined amount, and the process of obtaining the quantitative values of the composition and/or the thickness of the thin film after change of the estimated measured intensity by the fundamental parameter method is repeated, while changing the measurement line of which the estimated measured intensity is to be changed; and the quantitative error is estimated and/or the possibility of analysis is determined, and the optimum combination of the measurement lines is selected, on the basis of the obtained quantitative values and the specified composition and/or the specified thickness.

That is, by considering the fact that the intensities of the measurement lines greatly depend on both the composition and the thickness of the thin film, not only the quantitative error is estimated and/or the possibility of analysis is determined, but also the optimum combination of the measurement lines is selected. Accordingly, even in the case where both the composition and the thickness of each layer of the thin film are analyzed and the same elements are contained in different layers, appropriate measurement lines are automatically selected and accurate analysis can be performed.

Any combination of at least two constructions, disclosed in the appended claims and/or the specification and/or the accompanying drawings should be construed as included within the scope of the present invention. In particular, any combination of two or more of the appended claims should be equally construed as included within the scope of the present invention.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DESCRIPTION OF EMBODIMENTS

Figure 1:
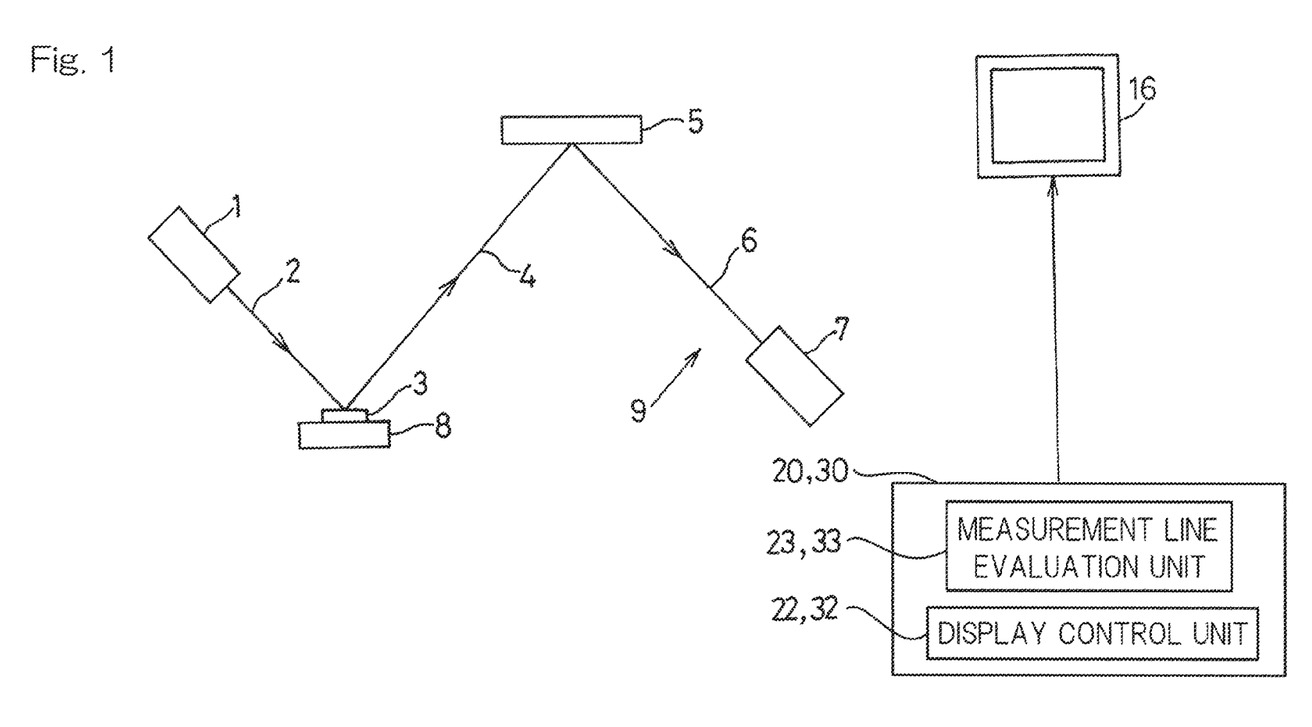
FIG. 1 is a schematic view of an X-ray fluorescence spectrometer according to a first or second embodiment of the present invention.

Hereinafter, a spectrometer according to a first embodiment of the present invention is described with reference to the drawings. As illustrated in FIG. 1, the spectrometer is an X-ray fluorescence spectrometer that irradiates, with primary X-rays 2 from an X-ray source 1 such as an X-ray tube, a sample 3 having a single-layer or multi-layer thin film formed independently or on a substrate, measures intensities of generated secondary X-rays 4 by using detection unit 9, and obtains quantitative values of a composition and/or a thickness of the thin film by a fundamental parameter method (hereinafter, also referred to as "FP method") on the basis of the measured intensities of the secondary X-rays 4. The spectrometer includes a measurement line evaluation unit 23 configured to estimate a quantitative error and/or determine possibility of analysis, for analysis using measurement lines 4 which are secondary X-rays of which the intensities are to be measured, and a display control unit 22 configured to cause a display 16 such as a liquid crystal display to display the quantitative error and/or the possibility of analysis obtained by the measurement line evaluation unit 23.

Here, the sample 3 is a so-called thin film sample such as an iron-zinc alloy plated steel sheet, and is placed on a sample stage 8. The detection unit 9 is composed of a spectroscopic device 5 which monochromates the secondary X-rays 4 such as fluorescent X-rays generated from the sample 3, and a detector 7 which measures the intensity of each of monochromated secondary X-rays 6. As the detection unit, a detector having a high energy resolution may be used without using the spectroscopic device 5. The display control unit 22 and the measurement line evaluation unit 23 are included in analysis condition creating unit 20.

Obtaining the quantitative values of the composition and/or the thickness of the thin film by an FP method on the basis of the measured intensities refers to calculating theoretical intensities of the secondary X-rays 4 generated from the sample 3 being excited by the primary X-rays 2 on the basis of a composition and/or a thickness assumed for each thin film (which may be a single layer) included in the sample 3, sequentially and approximately correcting and calculating the composition and/or the thickness assumed for each thin film such that the theoretical intensities match converted measured intensities which are obtained by converting the measured intensities of the sample 3 to theoretical intensity scale, and thereby obtaining the quantitative values of the composition and/or the thickness.

Figure 2:
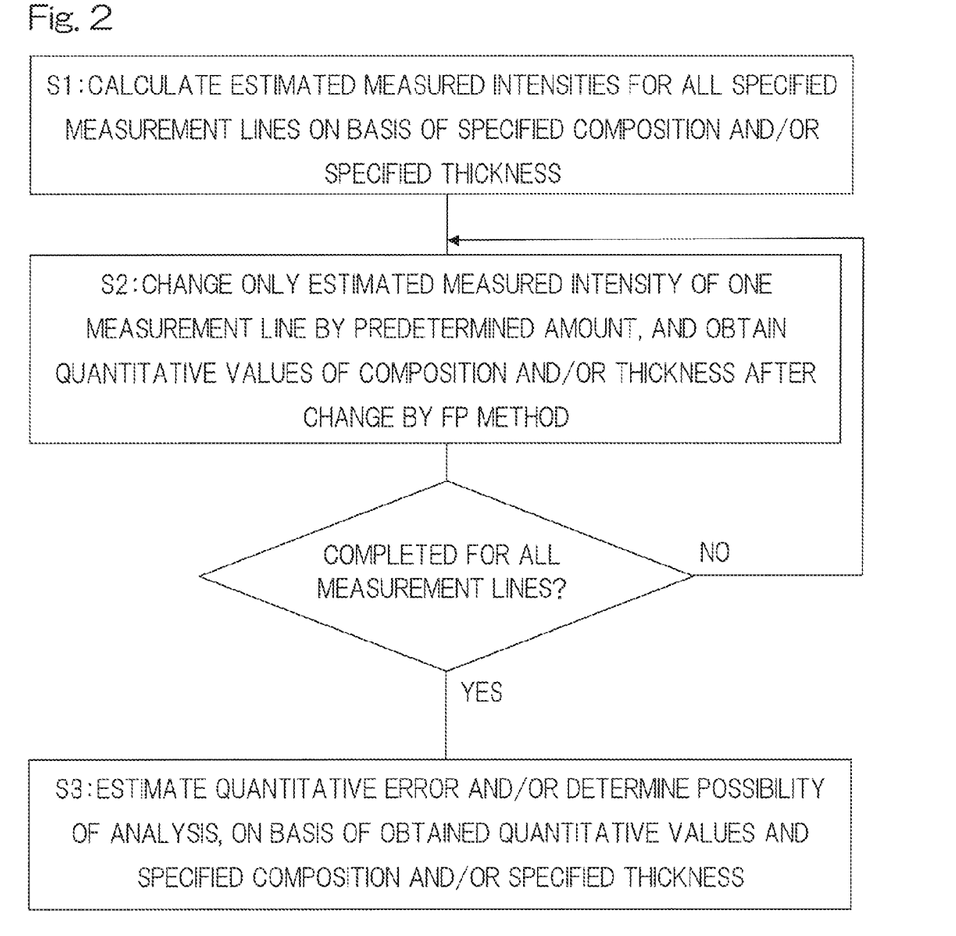
FIG. 2 is a flowchart showing operations of the X-ray fluorescence spectrometer according to the first embodiment.

Operations of the measurement line evaluation unit 23 included in the X-ray fluorescence spectrometer according to the first embodiment are specifically shown in the flowchart in FIG. 2. First, at step S1, the measurement line evaluation unit 23 calculates, on the basis of a composition Wi1 (the content ratio of each component) and/or a thickness Ti1 (reference numeral 1 indicates a specified numerical value) specified for the thin film i by an operator using an input unit (not illustrated) provided in the analysis condition creating unit 20, estimated measured intensities IipM1 (reference character M indicates a measured intensity scale) for all measurement lines ip which are similarly specified, by the theoretical intensity calculation and apparatus sensitivity. Each of the estimated measured intensities IipM1 is calculated by dividing, by the apparatus sensitivity kip, a theoretical intensity IipT1 (reference character T indicates a theoretical intensity scale) obtained for each measurement line ip by theoretical calculation, to convert to a measured intensity scale. The apparatus sensitivity kip is obtained in advance as the ratio of the theoretical intensity with respect to the measured intensity, by measuring, for each measurement line ip, a standard sample made of a pure substance, etc. and then is stored in the measurement line evaluation unit 23.

Next, at step S2, on the basis of a set of estimated measured intensities IipM2 obtained by changing, by a predetermined amount, only an estimated measured intensity of one measurement line among a set of the estimated measured intensities IipM1 calculated at step S1, a quantitative value Wi2(ip) of the composition and/or a quantitative value Ti2(ip) of the thickness (reference numeral 2 indicates a numerical value changed from a specified value) of the thin film after change of the estimated measured intensity is obtained by the FP method. More specifically, an accuracy Sip of the intensity of each measurement line ip is first estimated by the following equation (1).

$$Sip = (IipM1/t)^{1/2} \quad (1)$$

Here, t represents a measurement time (second), and is assumed to be 40 seconds, for example. Next, predetermined times ($\alpha$ times, e.g., two times) of the accuracy Sip are added to only an estimated measured intensity IipM1 of one measurement line ip among the set of the estimated measured intensities IipM1 calculated at step S1, by the following equation (2), to obtain an estimated measured intensity IipM2.

$$IipM2 = IipM1 + \alpha \times Sip \quad (2)$$

For the other measurement lines ip, the current measured intensities IipM1 are used as they are, as shown by the following equation (3).

$$IipM2 = IipM1 \quad (3)$$

A new set of the estimated measured intensities IipM2 is created from the estimated measured intensities IipM2 obtained by the equations (2) and (3). Subsequently, a quantitative value Wi2(ip) of the composition and/or a quantitative value Ti2(ip) of the thickness of the thin film after change of the estimated measured intensity is obtained by the FP method on the basis of the new set of the estimated measured intensities IipM2. The upper limit value (for example, two) may be set for the number of times of repeating calculation by the FP method to reach the quantitative value. This operation is performed while changing the estimated measured intensities of the measurement lines ip to IipM1+$\alpha \times$Sip one by one. That is, until the estimated measured intensities IipM1 of all the specified measurement lines ip are changed, the process at step S2 is repeated while changing a measurement line ip of which the estimated measured intensity IipM1 is to be changed. Variation in X-ray intensity of the measurement line is an independent phenomenon of each measurement line. Thus, the rationality is not impaired even if only the estimated measured intensity of each individual measurement line is changed.

Next, at step S3, on the basis of the quantitative value Wi2(ip) of the composition and/or the quantitative value Ti2(ip) of the thickness calculated at step S2 and the specified composition Wi1 and/or the specified thickness Ti1, quantitative errors $\Delta$Wi and/or $\Delta$Ti are estimated and/or possibility of analysis is determined. More specifically, for each measurement line ip of which the estimated measured intensity has been changed, a difference between the quantitative value Wi2(ip) of the composition and/or the quantitative value Ti2(ip) of the thickness after change and the specified composition Wi1 and/or the specified thickness Ti1 is first obtained by the following equations (4) and/or (5).

$$\Delta Wi(ip) = Wi2(ip) - Wi1 \quad (4)$$

$$\Delta Ti(ip) = Ti2(ip) - Ti1 \quad (5)$$

Next, for each thin film i, the quantitative error $\Delta$Wi of the composition and/or the quantitative error $\Delta$Ti of the thickness are estimated as root-mean-square error(s) represented by the following equations (6) and/or (7), considering all the specified measurement lines ip. Here, n represents the number of the measurement lines.

$$\Delta Wi = (\Sigma ip \Delta Wi(ip)^2 / n)^{1/2} \quad (6)$$

$$\Delta Ti = (\Sigma ip \Delta Ti(ip)^2 / n)^{1/2} \quad (7)$$

Instead of estimating the quantitative errors $\Delta$Wi and/or $\Delta$Ti, or in addition to estimating the quantitative errors $\Delta$Wi and/or ΔTi, the possibility of analysis using the specified measurement lines may be determined by the following equations (8) and/or (9).

$$\Delta Wi/Wi1 < Rs \quad (8)$$

$$\Delta Ti/Ti1 < Rs \quad (9)$$

Here, Rs represents a required relative accuracy, and is assumed to be uniformly 0.05, for example, but may be individually set for each thin film i. When the equations (8) and/or (9) are satisfied for the compositions and/or the thicknesses of all the thin films, it is determined that analysis is possible, and when the equations (8) and/or (9) are not satisfied for any one of the thin films, it is determined that analysis is impossible. The possibility of analysis may be determined for each of specified measurement lines by the following equations (10) and/or (11), and may be determined in the loop at step S2.

$$\Delta Wi(ip)/Wi1 < Rs \quad (10)$$

$$\Delta Ti(ip)/Ti1 < Rs \quad (11)$$

The quantitative errors ΔWi and/or ΔTi and/or the possibility of analysis obtained by the measurement line evaluation unit 23 in this way, are displayed on the display 16 by the display control unit 22. As described above, by considering the fact that the intensities of the measurement lines ip greatly depend on both the composition and the thickness of the thin film, the X-ray fluorescence spectrometer according to the first embodiment estimates the quantitative errors ΔWi and/or ΔTi, and/or determines the possibility of analysis, and displays the result on the display 16. Accordingly, even in the case where both the composition and the thickness of each layer of the thin film are analyzed and the same elements are contained in different layers, an operator can easily and appropriately select the measurement lines on the basis of the displayed result, thus enabling accurate analysis.

An X-ray fluorescence spectrometer according to a second embodiment of the present invention is described. As illustrated in FIG. 1, this spectrometer is an X-ray fluorescence spectrometer that irradiates, with the primary X-rays 2, a sample 3 having a single-layer or multi-layer thin film formed independently or on a substrate, and obtains quantitative values of a composition and/or a thickness of the thin film by an FP method on the basis of the measured intensities of generated secondary X-rays 4. The spectrometer includes a measurement line evaluation unit 33 configured to estimate a quantitative error and/or determine possibility of analysis, and to select an optimum combination of measurement lines which are secondary X-rays of which the intensities are to be measured, for analysis using the measurement lines 4, and a display control unit 32 configured to cause a display 16 to display the quantitative error and/or the possibility of the analysis, and the optimum combination of the measurement lines obtained by the measurement line evaluation unit 33.

The spectrometer according to the second embodiment differs from the spectrometer according to the first embodiment in operations of the measurement line evaluation unit 33 and operations of the display control unit 32, that is, what is displayed on the display 16. Thus, the explanation thereof is given.

Figure 3:
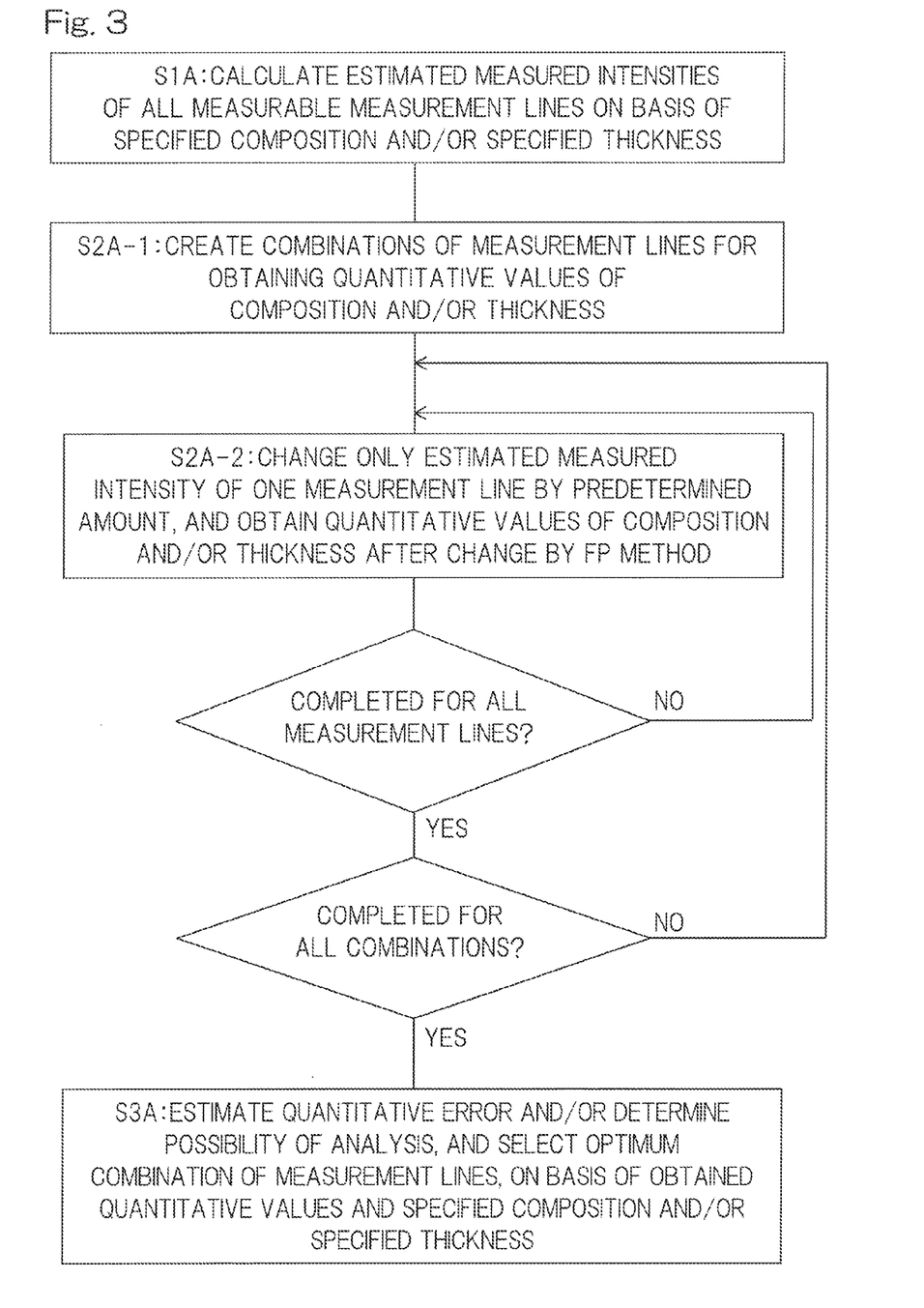
FIG. 3 is a flowchart showing operations of the X-ray fluorescence spectrometer according to the second embodiment.

Operations of the measurement line evaluation unit 33 included in the spectrometer according to the second embodiment are specifically shown in the flowchart in FIG. 3. At step S1A, for all the measurement lines ip of which the intensities can be measured, the estimated measured intensities IipM1 are calculated, as in the spectrometer according to the first embodiment, by the theoretical intensity calculation and the apparatus sensitivity on the basis of the composition Wi1 and/or the thickness Ti1 specified for the thin film i as in the spectrometer according to the first embodiment. For the measurement lines ip of which the intensities can be measured, a table of the measurement lines corresponding to elements contained in the thin film i stored in the measurement line evaluation unit 33 is searched on the basis of the configuration (for example, a spectroscopic device) of the spectrometer being used. For example, in a case where the sample 3 is an iron-zinc alloy plated steel sheet having a plated coat made of iron and zinc formed on a steel plate substrate, in which the specified composition Wi1 is the content ratio of iron, zinc is a residue, and the substrate is iron, six measurement lines ip, Zn—Kα, Zn—Kβ, Zn-Lα, Fe—Kα, Fe—Kβ, and Fe-Lα are retrieved in searching.

Next, at step S2A-1, combinations j of the measurement lines ip for obtaining the quantitative values of the composition and/or the thickness of the thin film are created from all the measurement lines ip which are retrieved at step S1A. In the above case, fifteen combinations are created because two measurement lines are used in order to analyze the iron content ratio and the thickness of the plated coat.

Next, at step S2A-2, for each combination j of the measurement lines ip created at step S2A-1, the quantitative value Wi2(ip,j) of the composition and/or the quantitative value Ti2(ip,j) of the thickness of the thin film after change of an estimated measured intensity is obtained by the FP method on the basis of a set of estimated measured intensities IipM2 obtained by changing, by a predetermined amount, only the estimated measured intensity of one measurement line among a set of the estimated measured intensities IipM1, which are calculated at step S1A, of the measurement lines ip included in the combination j, and such a process is repeated while changing a measurement line ip of which the estimated measured intensity IipM1 is to be changed. That is, for all the combinations j of the measurement lines ip created at step S2A-1, the operation at step S2 by the measurement line evaluation unit 23 of the spectrometer according to the first embodiment is performed.

Next, at step S3A, on the basis of the quantitative value Wi2(ip,j) of the composition and/or the quantitative value Ti2(ip,j) of the thickness obtained at step S2A-2 and the specified composition Wi1 and/or the specified thickness Ti1, the quantitative errors ΔWij and/or ΔTij are estimated and/or the possibility of analysis is determined, and the optimum combination of the measurement lines is selected. More specifically, for each of all the combinations j of measurement lines ip created at step S2A-1, each difference between the quantitative value Wi2(ip,j) of the composition and/or the quantitative value Ti2(ip,j) of the thickness after change and the specified composition Wi1 and/or the specified thickness Ti1 is first obtained, by the following equations (12) and/or (13), for each measurement line ip of which the estimated measured intensity has been changed.

$$\Delta Wi(ip,j) = Wi2(ip,j) - Wi1 \quad (12)$$

$$\Delta Ti(ip,j) = Ti2(ip,j) - Ti1 \quad (13)$$

Next, for each of all the combinations j of measurement lines ip created at step S2A-1, the quantitative error ΔWij of the composition and/or the quantitative error ΔTij of the thickness of each thin film i, are estimated by the following equations (14) and/or (15), considering all the combined measurement lines ip. Here, n represents the number of the measurement lines, as described above.

$$\Delta Wij = (\Sigma ip \Delta Wi(ip,j)^2/n)^{1/2} \quad (14)$$

$$\Delta Tij = (\Sigma ip \Delta Ti(ip,j)^2/n)^{1/2} \quad (15)$$

Furthermore, on the basis of the quantitative error $\Delta Wij$ of the composition and/or the quantitative error $\Delta Tij$ of the thickness estimated in this way, for example, a quantitative relative error $\Delta Wij/Wi1$ of the composition and/or a quantitative relative error $\Delta Tij/Ti1$ of the thickness are calculated for each combination j of the measurement lines ip. The largest numerical value of the quantitative relative errors is defined as the representative quantitative relative error of the combination j. Of all the combinations, a combination having the smallest representative quantitative relative error is selected as the optimum combination of the measurement lines.

The possibility of analysis may be determined for the selected optimum combination of the measurement lines by the above equations (8) and/or (9).

Also in this case, when the equations (8) and/or (9) are satisfied for the compositions and/or the thicknesses of all the thin films, it is determined that analysis is possible, and when the equations (8) and/or (9) are not satisfied for any one of those, it is determined that analysis is impossible. In each combination j of the measurement lines ip created at step S2A-2, the possibility of analysis may be determined for each measurement line ip by the above equations (10) and/or (11), and the process for the combination may be ended at a time point at which it is determined that analysis is impossible, to proceed to the process for a next combination.

The optimum combination of the measurement lines and the quantitative errors $\Delta Wij$ and/or $\Delta Tij$ of the optimum combination j and/or the possibility of analysis of the optimum combination j, which are obtained by the measurement line evaluation unit 33 in this way, are displayed on the display 16 by the display control unit 32. When analysis is impossible, a layer having an unanalyzable thickness and/or a component of which the content ratio is unanalyzable and a layer containing the unanalyzable component may be displayed on the display 16.

Table 1 shows the estimation result of quantitative errors by the measurement line evaluation unit 33 in a case of analyzing an iron-zinc alloy layer of an iron-zinc alloy plated steel sheet by using the spectrometer according to the second embodiment, as an example. In this example, the specified content ratio of Fe is 10.0% and the specified thickness is 4.3 μm. In addition, the number of the measurement lines of which the intensities can be measured is six, and fifteen combinations of the measurement lines are created, as described above. The change amount of the estimated measured intensity in the equation (2) is set to two times of the accuracy, and the lower limit of the relative accuracy of X-ray intensities is set to 0.05% considering various types of reproducibility. In Table 1, "RMS" indicates the quantitative error (the root-mean-square error) estimated by the equations (14) and (15), and "no solution" means that no quantitative value having a consistency between the content ratio and the thickness is obtained.

TABLE 1

| | Combination of Measurement Lines | | Measurement Line for | Thickness (μm) | | Fe mass % | |
|---|---|---|---|---|---|---|---|
| No. | Measurement Line 1 | Measurement Line 2 | Intensity Change | Quantitative Value | Error | Quantitative Value | Error |
| 1 | ZnKα | ZnKβ | ZnKα | 4.249 | −0.051 | 9.343 | −0.657 |
| | | | ZnKβ | 4.355 | 0.055 | 10.615 | 0.615 |
| | | | RMS | | 0.053 | | 0.636 |
| 2 | ZnKα | FeKα | ZnKα | 4.226 | −0.074 | 9.070 | −0.930 |
| | | | FeKα | 4.200 | −0.100 | 8.844 | −1.156 |
| | | | RMS | | 0.088 | | 1.049 |
| 3 | ZnKα | FeKβ | ZnKα | 4.257 | −0.043 | 9.442 | −0.558 |
| | | | FeKβ | 4.230 | −0.070 | 9.192 | −0.808 |
| | | | RMS | | 0.058 | | 0.694 |
| 4 | ZnKα | ZnLα | ZnKα | 4.306 | 0.006 | 10.000 | 0.000 |
| | | | ZnLα | 4.297 | −0.003 | 9.969 | −0.031 |
| | | | RMS | | 0.005 | | 0.022 |
| 5 | ZnKα | FeLα | ZnKα | 4.306 | 0.006 | 10.000 | 0.000 |
| | | | FeLα | 4.303 | 0.003 | 10.034 | 0.034 |
| | | | RMS | | 0.005 | | 0.024 |
| 6 | ZnKβ | FeKα | ZnKβ | 3.411 | −0.889 | 0.000 | −10.000 |
| | | | FeKα | 3.395 | −0.905 | 0.000 | −10.000 |
| | | | RMS | | 0.897 | | 10.000 |
| 7 | ZnKβ | FeKβ | ZnKβ | No Solution | | No Solution | |
| | | | FeKβ | 3.638 | −0.662 | 0.000 | 7.071 |
| | | | RMS | | | | |
| 8 | ZnKβ | ZnLα | ZnKβ | 4.306 | 0.006 | 10.000 | 0.000 |
| | | | ZnLα | 4.298 | −0.002 | 9.969 | −0.031 |
| | | | RMS | | 0.004 | | 0.022 |
| 9 | ZnKβ | FeLα | ZnKβ | 4.306 | 0.006 | 10.000 | 0.000 |
| | | | FeLα | 4.303 | 0.003 | 10.034 | 0.034 |
| | | | RMS | | 0.005 | | 0.024 |
| 10 | FeKα | FeKβ | FeKα | 4.408 | 0.108 | 11.560 | 1.560 |
| | | | FeKβ | 4.169 | −0.131 | 8.097 | −1.903 |
| | | | RMS | | 0.120 | | 1.740 |
| 11 | FeKα | ZnLα | FeKα | 4.293 | −0.007 | 10.000 | 0.000 |
| | | | ZnLα | 4.298 | −0.002 | 9.969 | −0.031 |
| | | | RMS | | 0.005 | | 0.022 |

TABLE 1-continued

| No. | Combination of Measurement Lines | | Measurement Line for Intensity Change | Thickness (μm) | | Fe mass % | |
|---|---|---|---|---|---|---|---|
| | Measurement Line 1 | Measurement Line 2 | | Quantitative Value | Error | Quantitative Value | Error |
| 12 | FeKα | FeLα | FeKα | 4.293 | −0.007 | 10.000 | 0.000 |
| | | | FeLα | 4.302 | 0.002 | 10.034 | 0.034 |
| | | | RMS | | 0.005 | | 0.024 |
| 13 | FeKβ | ZnLα | FeKβ | 4.292 | −0.008 | 10.000 | 0.000 |
| | | | ZnLα | 4.298 | −0.002 | 9.969 | −0.031 |
| | | | RMS | | 0.006 | | 0.022 |
| 14 | FeKβ | FeLα | FeKβ | 4.292 | −0.008 | 10.000 | 0.000 |
| | | | FeLα | 4.302 | 0.002 | 10.034 | 0.034 |
| | | | RMS | | 0.006 | | 0.024 |
| 15 | ZnLα | FeLα | ZnLα | No Solution | | No Solution | |
| | | | FeLα | No Solution | | No Solution | |
| | | | RMS | | | | |

The combination of Zn—Kβ and Zn-Lα in which the quantitative errors RMS estimated for the content ratio and the thickness are both minimum in Table 1, is selected as the optimum combination of the measurement lines, by the measurement line evaluation unit 33, and this fact is displayed on the display 16 by the display control unit 32.

As described above, by considering the fact that the intensities of the measurement lines greatly depend on both the composition and the thickness of a thin film, the X-ray fluorescence spectrometer according to the second embodiment not only estimates the quantitative errors and/or determines the possibility of analysis, but also selects the optimum combination of the measurement lines. Accordingly, even in the case where both the composition and the thickness of each layer of the thin film are analyzed and the same elements are contained in different layers, appropriate measurement lines are automatically selected, thus enabling accurate analysis.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

REFERENCE NUMERALS

2 . . . primary X-rays
3 . . . sample
4 . . . secondary X-rays (measurement lines)
16 . . . display
22, 32 . . . display control unit
23, 33 . . . measurement line evaluation unit

What is claimed is:

1. An X-ray fluorescence spectrometer which irradiates, with primary X-rays, a sample having a single-layer or multi-layer thin film formed independently or on a substrate, and obtains quantitative values of a composition and/or a thickness of the thin film by a fundamental parameter method on the basis of measured intensities of generated secondary X-rays, the spectrometer comprising:

a measurement line evaluation unit configured to estimate a quantitative error and/or to determine possibility of analysis, for analysis using measurement lines which are secondary X-rays of which the intensities are to be measured; and a display control unit configured to cause a display to display the quantitative error and/or the possibility of analysis obtained by the measurement line evaluation unit, wherein the measurement line evaluation unit calculates, for all specified measurement lines, estimated measured intensities by theoretical intensity calculation and apparatus sensitivity on the basis of a composition and/or a thickness specified for the thin film, repeats a process for each measurement line among the specified measurement lines of:

changing, by a predetermined amount, only an estimated measured intensity of one measurement line among a set of the calculated estimated measured intensities, and obtaining, on the basis of a set of estimated measured intensities obtained by the changing, quantitative values of the composition and/or the thickness of the thin film by the fundamental parameter method, and estimates the quantitative error and/or determines the possibility of analysis, on the basis of the obtained quantitative values and the specified composition and/or the specified thickness.

2. An X-ray fluorescence spectrometer which irradiates, with primary X-rays, a sample having a single-layer or multi-layer thin film formed independently or on a substrate, and obtains quantitative values of a composition and/or a thickness of the thin film by a fundamental parameter method on the basis of measured intensities of generated secondary X-rays, the spectrometer comprising:

a measurement line evaluation unit configured to estimate a quantitative error and/or determine possibility of analysis, and to select an optimum combination of measurement lines which are secondary X-rays of which the intensities are to be measured, for analysis using the measurement lines; and a display control unit configured to cause a display to display the quantitative error and/or the possibility of analysis, and the optimum combination of the measurement lines obtained by the measurement line evaluation unit, wherein the measurement line evaluation unit
- calculates, for all the measurement lines of which the intensities can be measured, estimated measured intensities by theoretical intensity calculation and apparatus sensitivity on the basis of a composition and/or a thickness specified for the thin film,
- creates combinations of the measurement lines for obtaining the quantitative values of the composition and/or the thickness of the thin film, from all the measurement lines of which the intensities can be measured,
- repeats, for each combination of the measurement lines, a process for each measurement line included in a combination of:
  - changing, by a predetermined amount, only the estimated measured intensity of one measurement line among a set of the calculated estimated measured intensities of the measurement lines included in the combination, and
  - obtaining, on the basis of a set of estimated measured intensities obtained by the changing, quantitative values of the composition and/or the thickness of the thin film, by the fundamental parameter method, and
- estimates the quantitative error and/or determines the possibility of analysis, and selects an optimum combination of the measurement lines, on the basis of the obtained quantitative values and the specified composition and/or the specified thickness.

* * * * *